US 8,986,235 B2

(12) United States Patent
Weaver, II et al.

(10) Patent No.: US 8,986,235 B2
(45) Date of Patent: Mar. 24, 2015

(54) ANKLE BRACE

(75) Inventors: Edward L. Weaver, II, Milford, OH (US); John R. Elrod, Cincinnati, OH (US)

(73) Assignee: 3M Innovative Properties Company, St. Paul, MN (US)

( * ) Notice: Subject to any disclaimer, the term of this patent is extended or adjusted under 35 U.S.C. 154(b) by 427 days.

(21) Appl. No.: 13/262,172

(22) PCT Filed: Mar. 29, 2010

(86) PCT No.: PCT/US2010/029050
§ 371 (c)(1),
(2), (4) Date: Sep. 29, 2011

(87) PCT Pub. No.: WO2010/117723
PCT Pub. Date: Oct. 14, 2010

(65) Prior Publication Data
US 2012/0029404 A1    Feb. 2, 2012

Related U.S. Application Data

(60) Provisional application No. 61/165,337, filed on Mar. 31, 2009.

(51) Int. Cl.
*A61F 5/00* (2006.01)
*A61F 13/00* (2006.01)
*A61F 5/01* (2006.01)

(52) U.S. Cl.
CPC .................................. *A61F 5/0111* (2013.01)
USPC ........ 602/65; 602/5; 602/60; 602/61; 602/62; 602/66

(58) Field of Classification Search
USPC .......... 602/5, 23, 27–29, 60–65, 66; 128/882, 128/845; D24/190–192; 36/8.1–8.3, 30, 88; D2/980, 989, 902
See application file for complete search history.

(56) References Cited

U.S. PATENT DOCUMENTS

| 851,950 A | 4/1907 | Le Mat |
| 1,027,897 A | 5/1912 | Quenzer |
| 1,037,441 A | 9/1912 | Collis |
| 1,081,366 A | 12/1913 | Collis |
| 3,028,861 A | 4/1962 | Shapiro |
| 3,298,365 A | 1/1967 | Lewis |
| 3,970,083 A | 7/1976 | Carrigan |
| 4,187,844 A | 2/1980 | Caprio |
| 4,237,874 A | 12/1980 | Nelson |

(Continued)

FOREIGN PATENT DOCUMENTS

| EP | 820741 | 1/1998 |
| JP | H04-77911 U | 7/1992 |

(Continued)

OTHER PUBLICATIONS

International Search Report for PCT/US2010/029050, 3 pages.

*Primary Examiner* — Kim M Lewis
(74) *Attorney, Agent, or Firm* — Kevin W. Weber; Lisa P. Fulton

(57) ABSTRACT

An ankle brace is provided that includes (a) a boot assembly having a semi-rigid or rigid support, (b) an adjustable stirrup configured to go under the arch of a wearer's foot, and (c) a lace and rotatable tightening mechanism configured to tighten the adjustable stirrup and pull it upward.

18 Claims, 3 Drawing Sheets

(56) References Cited

U.S. PATENT DOCUMENTS

| | | | |
|---|---|---|---|
| 4,280,488 A | 7/1981 | Polsky | |
| 4,527,556 A | 7/1985 | Nelson | |
| 4,651,726 A | 3/1987 | Holland | |
| 4,724,847 A | 2/1988 | Nelson | |
| 4,825,856 A | 5/1989 | Nelson | |
| 4,878,504 A | 11/1989 | Nelson | |
| 4,936,295 A | 6/1990 | Crane | |
| 4,960,135 A | 10/1990 | Nelson | |
| 5,000,195 A | 3/1991 | Neal | |
| 5,007,417 A | 4/1991 | Bender | |
| 5,014,691 A | 5/1991 | Cueman | |
| 5,341,583 A | 8/1994 | Hallenbeck | |
| 5,449,341 A * | 9/1995 | Harris | 602/63 |
| 5,657,767 A | 8/1997 | Nelson | |
| 5,681,271 A | 10/1997 | Nelson | |
| D388,173 S | 12/1997 | Eriksson | |
| 5,741,222 A | 4/1998 | Fiore | |
| D394,112 S | 5/1998 | Duback | |
| 5,795,316 A * | 8/1998 | Gaylord | 602/27 |
| 5,853,381 A | 12/1998 | Stevenson | |
| 5,868,693 A * | 2/1999 | Duback et al. | 602/27 |
| 5,934,599 A * | 8/1999 | Hammerslag | 242/396.1 |
| 5,944,678 A | 8/1999 | Hubbard | |
| 6,155,997 A | 12/2000 | Castro | |
| 6,394,971 B1 | 5/2002 | Slautterback | |
| 6,398,750 B1 | 6/2002 | Quinn | |
| 6,540,705 B2 | 4/2003 | Norstrem | |
| 6,602,215 B1 | 8/2003 | Richie | |
| 6,652,474 B1 | 11/2003 | Quinn | |
| 6,663,583 B1 | 12/2003 | Janis | |
| 7,014,621 B2 | 3/2006 | Nelson | |
| D552,744 S | 10/2007 | Verkade | |
| 7,497,839 B2 | 3/2009 | Quinn | |
| 7,651,472 B2 | 1/2010 | Gaylord | |
| D639,965 S * | 6/2011 | Wehsely-Swiczinsky | D24/192 |
| D649,651 S | 11/2011 | Weaver | |
| 2006/0004310 A1 | 1/2006 | Parizot | |
| 2006/0004311 A1 | 1/2006 | Hargrave | |
| 2006/0052734 A1 | 3/2006 | Evans | |
| 2006/0156517 A1 | 7/2006 | Hammerslag | |
| 2007/0169378 A1 | 7/2007 | Sodeberg | |
| 2008/0066272 A1 | 3/2008 | Hammerslag | |
| 2010/0036306 A1* | 2/2010 | Lussier et al. | 602/65 |
| 2011/0144554 A1* | 6/2011 | Weaver, II et al. | 602/27 |
| 2013/0012856 A1* | 1/2013 | Hammerslag et al. | 602/27 |
| 2013/0317404 A1* | 11/2013 | Bauer et al. | 602/27 |
| 2014/0276318 A1* | 9/2014 | Faux | 602/28 |

FOREIGN PATENT DOCUMENTS

| | | |
|---|---|---|
| JP | 3072845 | 11/2000 |
| KR | 10-2007-0078568 | 8/2007 |
| WO | WO 2005/087150 A1 | 9/2005 |
| WO | WO 2005-117773 | 12/2005 |
| WO | WO 2007-051524 | 5/2007 |
| WO | WO 2008-033963 | 3/2008 |
| WO | WO 2009-140165 | 11/2009 |
| WO | WO 2010-117749 | 10/2010 |

\* cited by examiner

ANKLE BRACE

CROSS REFERENCE TO RELATED APPLICATIONS

This application is a national stage filing under 35 U.S.C. 371 of PCT/US2010/029050, filed Mar. 29, 2010, which claims priority to Provisional Application No. 61/165,337, filed Mar. 31, 2009, the disclosure of which is incorporated by reference in its/their entirety herein.

FIELD

This invention relates to an ankle brace with an adjustable stirrup.

BACKGROUND

Ligaments in the ankle can be injured when a greater than normal stretching force is applied to them. This can happen when the foot is turned inward or inverted. Once this type of injury occurs, the ankle can become instable for some period of time and the risk of re-injury is high. Repeated injuries can result in chronic ankle instability.

One solution that has been relatively successful in stabilizing the ankle against inversion is taping the ankle in a manner to prevent rotation of the foot in a direction that would strain the ligaments, particularly if they are already in a weakened condition Ankle taping includes three primary components: (1) anchor strips around the leg below the calf, (2) a heel lock at about a 45° angle, and (3) an ankle stirrup, which starts on one side of the ankle (for example, the medial side), goes under the arch of the foot, and back up the other side of the ankle (for example, the lateral side).

The application of adhesive tape by trainers or coaches can be expensive, however, both in terms of staff time and in terms of the quantity of tape applied and discarded. Furthermore, tape can loosen, be uncomfortable to remove, and/or leave a sticky residue. It can also be difficult to adjust the amount of compression or support provided by tape (that is, to loosen or tighten tape) after it has been applied.

To avoid these difficulties, numerous reusable ankle braces have been developed. Such ankle braces are typically secured to the ankle using laces, buckles, and/or hook and loop closures (for example, Velcro™). But, ankle braces comprising these types of closure systems tend to lose tension or loosen over time during use. For example, buckles can slide, laces can elongate, and hook and loop closures can loosen.

SUMMARY

In view of the foregoing, we recognize that there is a need in the art for ankle braces that stabilize the ankle against inversion like taping yet do not loosen over time during use. In addition, we recognize that it would be advantageous if such ankle braces could be quickly loosened and retightened so that, depending upon the task at hand, users could adjust the ankle brace accordingly.

Briefly, in one aspect, the present invention provides an ankle brace comprising (a) a boot assembly comprising a semi-rigid or rigid support, (b) an adjustable stirrup configured to go under the arch of a wearer's foot, the adjustable strap being located at least partially within the boot assembly, (c) a first lace threaded through each end of the adjustable stirrup, and (d) a first rotatable tightening mechanism configured to apply tension on the lace thereby tightening the adjustable stirrup and pulling it upward.

The ankle braces of the present invention meet the need in the art for ankle braces that stabilize the ankle against inversion. The adjustable stirrup mimics the stirrup utilized in conventional taping. Furthermore, the lacing system of the present invention, which includes a rotatable tightening mechanism, can be quickly and easily loosened and retightened so that the user can adjust the ankle brace as needed.

DETAILED DESCRIPTION

Figure 1:
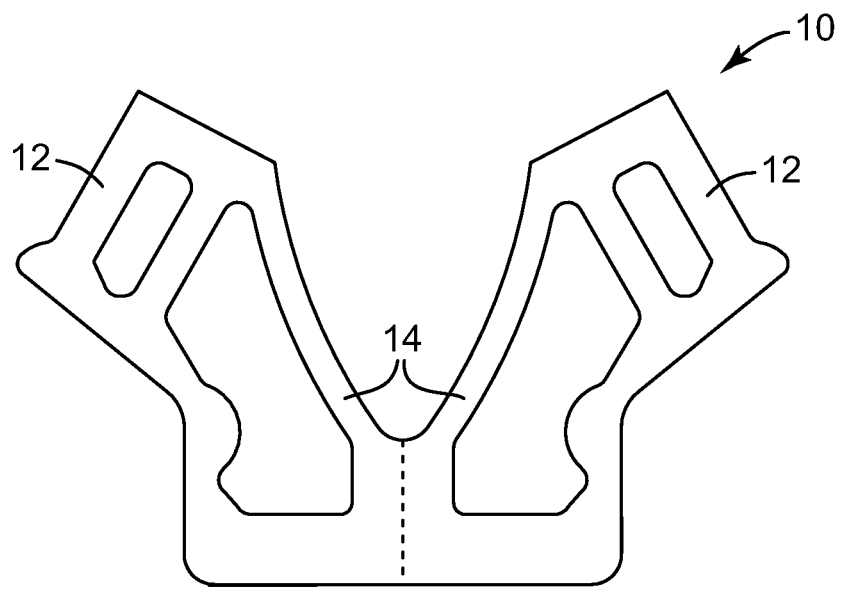
FIG. 1 is a schematic representation of a flat view of a support structure useful in ankle braces of the invention.

The ankle braces of the present invention include an adjustable stirrup configured to extend down one side of a user's ankle (for example, the medial side), go under the arch of the user's foot, and back up the other side of the user's ankle (for example, the lateral side). This stirrup mimics the ankle stirrup utilized in traditional ankle taping. The adjustability of the stirrup is provided by a reel and lace system. The reel and lace system includes a lace or cable that is threaded through a portion of each end of the stirrup and attached at opposite ends to a tightening mechanism as described in further detail below. As used herein, the terms lace and cable have the same meaning unless specified otherwise. The lace is preferably a low friction lace that slides relatively easily through the brace.

The adjustable stirrup typically comprises a substantially non-stretchy or inelastic material (for example, having no more than about 60% stretch under tension). It can be made substantially rigid or non-rigid, depending upon the number of layers and materials utilized (for example, non-wovens, plastics, etc.). In some embodiments, the adjustable stirrup comprises a substantially non-stretchy fabric.

Some examples of useful materials for the adjustable stirrup include nylon strapping, flexible plastics such as polyethylenes and thermoplastic polyurethanes, and other materials having similar tensile strengths. Preferably the adjustable stirrup comprises nylon, thermoplastic polyurethane, or polyethylene. Typically the stirrup is between about 20 cm and about 30 cm long, and between about 2 cm and about 5 cm long.

The adjustable stirrup is typically at least partially inside a boot assembly. It can, for example, be situated inside a boot assembly such that the stirrup is in contact with the skin when the ankle brace is worn. In other embodiments, the stirrup can be situated, or partially situated, between layers of the boot assembly.

The boot assembly will typically have a heel cut-out to provide improved fit and comfort. The boot assembly can comprise a simple one piece bootie. Typically, however, the boot assembly will comprise a bootie portion and a tongue portion. The bootie portion can be secured across the tongue portion using conventional securing means or a reel and lace system as described below. In some embodiments, the tongue is completely removable from the brace. In some embodiments, the tongue may be configured such that it allows complete opening of the brace while not being completely separated from the brace.

The boot assembly can be constructed from one or more relatively conformable materials such as a layer of foam (for example, open-cell foam). The inside of the boot assembly (that is, the part of the boot assembly that is in contact with the skin when the ankle brace is worn) preferably comprises a material that is comfortable against the skin such as polyester or cotton.

The boot assembly comprises a semi-rigid or rigid support that prevents the boot assembly from collapsing when tension is applied to the adjustable stirrup. The support is typically a nonwoven material such as a flexible plastic. Preferably, the support comprises thermoplastic polyurethane. The support may be disposed within the boot assembly or on the outer surface of the boot assembly. It can, for example, be sewn, glued, or heat sealed on to the outer surface of the boot assembly. Alternatively, it may be positioned between layers of the boot assembly such that it is not visible to the wearer.

Figure 2:
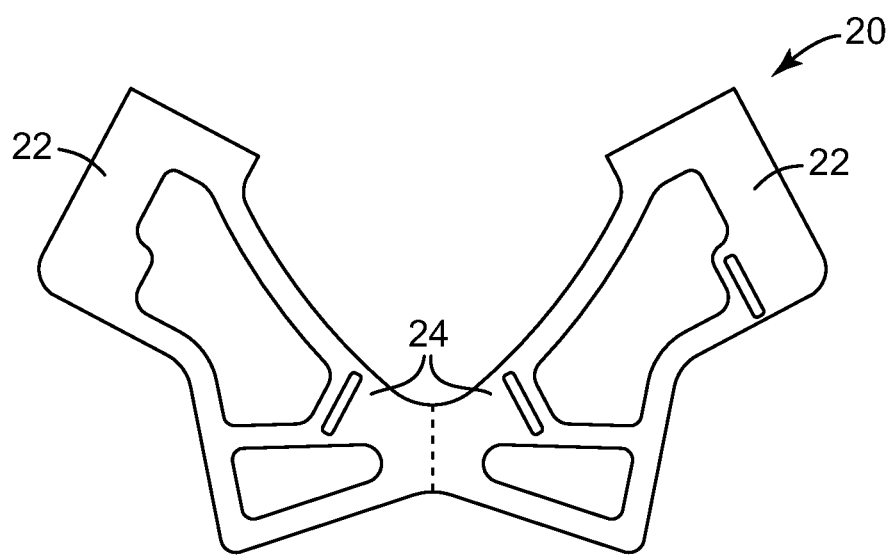
FIG. 2 is a schematic representation of a flat view of another support structure useful in ankle braces of the invention.

In some embodiments, the support is a support structure that mimics the anchor and heel lock of conventional taping methods. FIGS. 1 and 2 illustrate flat views of support structures 10 and 20. Anchor portions 12 and 22 mimic the anchor of conventional taping methods and heel lock portions 14 and 24 mimic the heel lock of conventional taping methods. Support structures 10 and 20 also provide support to the boot assembly and prevent it from collapsing when tension is applied to the adjustable stirrup. In some embodiments, support structures 10 and 20 are split into to separate pieces.

In one embodiment, the boot assembly comprises a three layer construction comprising a flexible plastic (preferably, thermoplastic polyurethane) support sandwiched between two other layers of foam laminates and nylon.

Preferably, the boot assembly, or at least a major portion of the boot assembly, is breathable (for example, has a moisture vapor transmission rate (MVTR) greater than about 3000 grams per square meter per 24 hours).

Preferably, the outer surfaces of the boot assembly are relatively low friction in order to facilitate sliding of the lace over the surfaces when the lace is tightened or loosened. The low friction surfaces may be formed integrally with the boot assembly or may be applied thereto by adhesives, heat bonding, stitching, or the like. The outer surfaces of the boot assembly can comprise, for example, spacer fabric, foam laminate, rip-stop nylon, a nylon fabric of 70 denier or higher, or combinations thereof.

Spacer fabric is a laminate that is knitted concurrently. This knitting method provides the ability to manipulate the layers individually to exhibit independent properties. For example, an inner layer can be of a smooth, skin-friendly polyester; a center layer, which is vertical (that is, perpendicular to the inner and outer layers), can be a nylon or monofilament layer that by increasing or decreasing the count per square inch provides more or less density in the overall laminate; and an outer surface can be a nylon to provide wicking of moisture and increased wear resistance. The outer surface of a spacer fabricate visually appears to be porous. Spacer fabricate is available, for example, from Gehring Textiles, Inc. (Garden City, N.Y.) and Eastex Products, Inc. (Holbrook, Mass.).

Rip-stop nylon is a light-weight nylon fabric with interwoven ripstop reinforcement threads in a crosshatch pattern.

In some preferred embodiments, the boot assembly comprises a spacer fabric as the primary outer surface. In some preferred embodiments, the inner liner of the boot assembly is a urethane foam laminate that provides padding (resilience) against the components of the ankle brace to provide comfort to the user and to avoid pressure points.

The stirrup lace can be threaded through a loop at the top of each end of the stirrup (for example, created by folding over each end of the stirrup and stitching a loop). Alternatively, the lace can be threaded through stirrup lace guides attached to each end of the stirrup. Stirrup lace guides can also be inserted into loops created as described above. The lace slides through the loops or stirrup lace guides during tightening and untightening of stirrup as described in more detail below.

Preferably, the boot assembly includes additional lace guides to guide the laces into the stirrup lace guides and back to the tightening mechanism. These additional lace guides can, for example, be attached to the outer surface of the boot assembly or they may be partially or completely sandwiched between layers of the boot assembly (for example, in a generally tube-like shape). Lace guides can be attached to the boot assembly in any of a variety of ways, as will be appreciated by those of skill in the art. For example, the lace guides can be sewn directly to the boot assembly or the stirrup.

Preferably, all of the lace guides are constructed of rigid materials that resist bending. They are also preferably constructed from low friction materials such as a lubricious polymer or metal that facilitates the sliding of the lace therethrough. Alternatively, the lace guides can be made from any convenient substantially rigid material, and can then be coated with a lubricious coating on at least the sliding portion in order to decrease friction.

Preferably, each of the lace guides defines a pair of openings that communicate with opposite ends of a lumen extending therethrough. The openings are preferably at least as wide as the cross-section of the lumen. Alternatively, the lace guides can comprise an open channel having, for example, a semicircular or "U" shaped cross-section. Examples of lace guides or "guide members" are described in greater detail in U.S. Patent Publication Nos. 2006/0156517 and 2007/0169378.

The lace may be formed from any of a wide variety of polymeric or metal materials or combinations thereof that exhibit sufficient axial strength and bendability for the present application. For example, any of a wide variety of solid core wires, solid core polymers, or multi-filament wires or polymers, which may be woven, braided, twisted or otherwise configured, can be used. A solid or multi-filament metal core can be provided with a polymeric coating such as polytetrafluoroethylene (PTFE) or others known in the art in order to reduce friction. In one embodiment, the lace comprises a stranded cable such as a 7 by 7 strand cable manufactured of stainless steel. In order to reduce friction between the lace and the lace guides through which the lace slid, the outer surface of the lace is preferably coated with a lubricious material such as nylon or PTFE. In a preferred embodiment, the diameter of the lace ranges from about 0.024 inches to about 0.060 inches and is preferably 0.032 inches. The lace is desirably strong enough to withstand loads of at least about 40 pounds and preferably at least about 90 pounds. In certain embodiments, the lace is rated from about 100 pounds up to as high as about 200 pounds or more.

The stirrup tightening mechanism is mounted to the ankle brace. The tightening mechanism can be located at any variety of locations on the brace. A preferred location is on the back of the brace (that is, such that it is located on the backside of the user's leg when worn). Location of the stirrup tightening mechanism may be optimized in view of a variety of considerations including overall brace design. The shape and overall volume of the stirrup tightening mechanism can be varied depending, for example, upon the gear train design. A relatively low-profile stirrup tightening mechanism is generally preferred. The mounted profile of the stirrup tightening mechanism can be further reduced by recessing the tightening mechanism into the outer surface of the brace.

In general, the stirrup tightening mechanism comprises a control such as a lever, crank or knob, which can be manipulated to retract the lace. In addition, the stirrup tightening mechanism preferably comprises a mechanism of release such as a button or lever for disengaging the stirrup tightening mechanism to permit the lace to be withdrawn freely. In some embodiments, the stirrup tightening mechanism is released by pulling outwards on the control. In some embodiments, an additional lock may be provided in the form of, for example, a button or lever that must be actuated to allow the control to be, for example, pulled outwards to release the system.

The stirrup tightening mechanism generally comprises a housing and a circular knob rotatably mounted thereto. The knob may be rotated to wind the ends of the lace into the housing and thereby provide the final tension to the lace to reduce the slack and provide the desired level of tightness. As the slack in the lace reduces, the lace pulls the stirrup upwards, tightening the stirrup to provide more support to the wearer. The knob may also be rotated through the use of a tool or small motor attached to the knob. Examples of various tightening mechanisms suitable for this task are disclosed in greater detail in U.S. Patent Publication Nos. 2006/0156517 and 2007/0169378. Suitable tightening mechanisms are available from Boa Technology, Inc. (Steamboat Springs, Colo.).

In some embodiments of the invention, the stirrup tightening mechanism is also used to tighten the lower half of the ankle brace (that is, the portion of the brace that is below the functional axis or pivot point of the ankle when worn). The stirrup tightening mechanism can be used, for example, to tighten the ankle brace around the foot by drawing the opposing sides of the brace towards one another (preferably over the tongue) by utilizing a lacing system that draws the opposing sides of the lacing system toward each other.

In such embodiments, the lace that is used to tighten the stirrup is also threaded through opposing lacing guides on the lower opposing sides of the brace. The laces may be threaded in a crossing pattern along a forward-facing portion of the brace between two generally parallel rows of side retaining guide members. The side retaining guide members may consist of a strip of material attached to the brace so as to define a space in which guides are positioned. The lace slides through the guides during tightening and untightening of the lace. The number of retaining guide members may vary. Preferably, the lace slides through guides on the tongue of the brace and maintains a connection between the tongue and the bootie portion of the brace when the brace is in its open configuration.

The laces do not have to be threaded in a crossing pattern in the lacing zone. As will be apparent to those of skill in the art, it is possible to configure the lacing system such that the lace passes across the outer surface of the brace in a substantially parallel, uncrossed path. Such substantially parallel lacing configurations are disclosed in greater detail in U.S. Patent Publication No. 2008/0066272.

In embodiments wherein the stirrup tightening mechanism is also used for the lower half of the ankle brace, as the stirrup/lower lace system is tightened, the stirrup will be tightened and the spacing distance between opposing guide members in the lower portion of the brace will be reduced. The wearer, however, may prefer to tighten only the stirrup or only the lower portion of the brace. Therefore, in some embodiments of the invention, two separate lacing systems/tightening mechanisms can be utilized for tightening the stirrup and tightening the lower portion of the brace.

Additionally or alternatively, in some embodiments, a separate lacing system and tightening mechanism is utilized to tighten the upper portion of the ankle brace (that is, the portion of the brace that is above the functional axis or pivot point of the ankle when worn). In such embodiments, a lace can be threaded through opposing lacing guides on the upper opposing sides of the brace. The lace may be threaded in a crossing pattern along a forward-facing portion of the brace between two generally parallel rows of side retaining guide members. A crossing pattern is not required, however. The number of retaining guide members may vary. Preferably, the lace slides through guides on the tongue of the brace and maintains a connection between the tongue and the bootie portion of the brace when the brace is in its open configuration.

In embodiments having a separate lacing system for the upper portion of the ankle the tightening mechanism is preferably located on the tongue of the brace or one of the sides of the brace.

Figure 3:
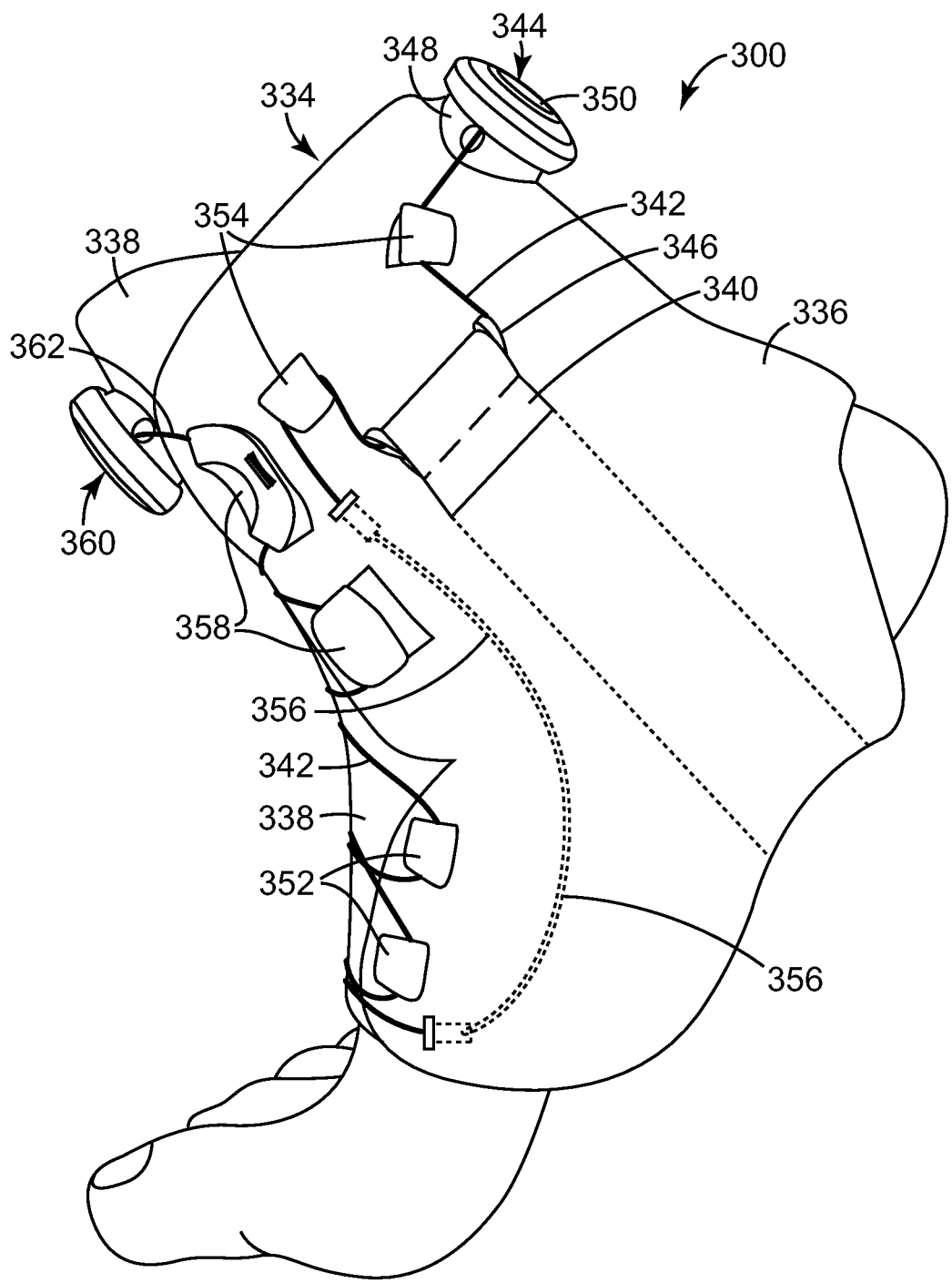
FIG. 3 is a perspective view of one embodiment of the ankle brace of the invention.

FIG. 3 illustrates an ankle brace of the invention that has one lacing system and tightening mechanism for tightening the stirrup and the lower portion of the brace and a second lacing system and tightening mechanism for tightening the upper portion of the brace.

Ankle brace 300 comprises boot assembly 334 with a support structure disposed therein (not shown). Boot assembly 334 has a bootie portion 336 and a tongue portion 338. Adjustable stirrup 340 is configured within bootie portion 336 to extend down one side of a user's ankle, go under the arch of the user's foot, and back up the other side of the user's ankle. The majority of stirrup 340 is inside boot assembly 334. The adjustability of stirrup 340 is provided by a reel and lace system that includes lace 342 and tightening mechanism 344. Lace 342 is attached at opposite ends to tightening mechanism 344 and is threaded through stirrup lace guide 346. Tightening mechanism 344 is mounted at the back of boot assembly 334 such that it is located on the backside of the user's leg when the brace is worn. It comprises housing 348 and circular knob 350 mounted thereto.

Lace 342 and tightening mechanism 344 are also configured to tighten the lower half of ankle brace 300 (that is, the portion of the brace that is below the functional axis of ankle when worn). Lace 342 is threaded in a crossing pattern along a forward facing portion of the brace through opposing lacing guides 352 on the lower portion of boot assembly 334. Additional lacing guides 354 and tube-like lacing guide 356 (embedded within bootie portion 336) help to guide lace 342 to and from tightening mechanism 344, stirrup 340 and opposing lacing guides 352. Lace 342 slides through opposing lacing guides 352 during tightening and untightening of the lace.

A separate lacing system and tightening mechanism is utilized to tighten the upper portion of ankle brace 300 (that is, the portion of the brace that is above the functional axis of the ankle when worn). A second lace 362 is threaded through opposing lacing guides 358 on the upper portion of boot assembly 334 and attached at opposite ends to second tightening mechanism 360 located on tongue portion 338.

Figure 4:
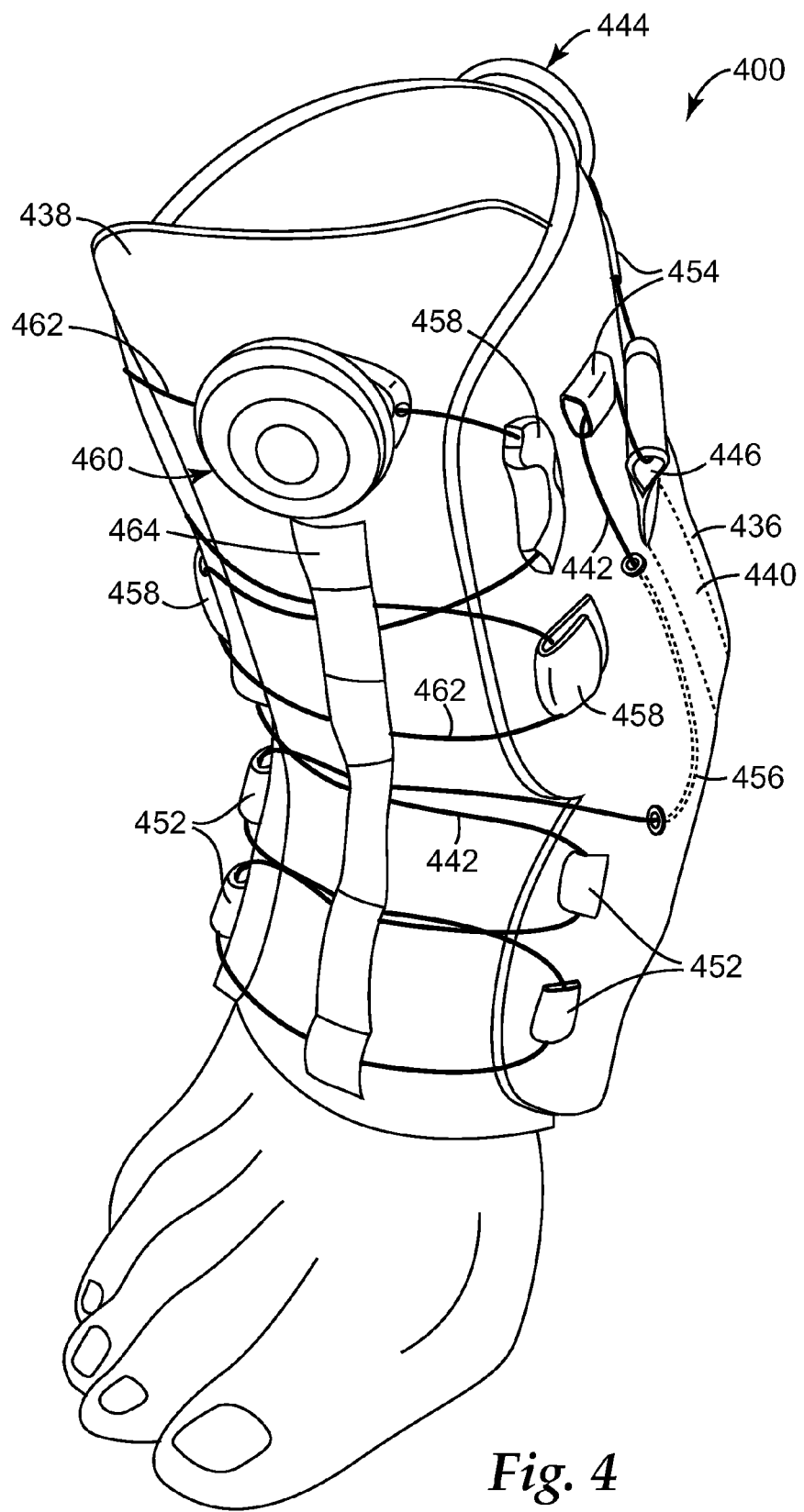
FIG. 4 is a perspective view of another embodiment of the ankle brace of the invention.

FIG. 4 illustrates another ankle brace of the invention that has one lacing system and tightening mechanism for tightening the stirrup and the lower portion of the brace and a second lacing system and tightening mechanism for tightening the upper portion of the brace Ankle brace 400 is similar to ankle brace 300 and the same numbering system is utilized to denote common features. Ankle brace 400 accordingly includes: a stirrup 440; a tightening mechanism 444; a stirrup lace guide 446; an opposing lacing guides 452; additional lacing guides 454; tube-like lacing guide 456; second opposing lacing guides 458; and a second tightening mechanism 460. Ankle brace 400 differs from ankle brace 300 in that lace 442 and 462 slide through tongue lace guide 464 on the tongue portion 438 and maintain a connection between tongue portion 438 and bootie portion 436 of the brace when it is in open configuration.

When the ankle braces of the present invention comprise two or more separate tightening mechanisms, the wearer may tighten certain portions of the brace more than others. That is, the brace is capable of zonal tightening wherein different zones may have different tightness. Examples of zonal tightening are described in greater detail in U.S. Patent Publication No. 2006/0156517.

In some embodiments, the guides placed in the middle of the brace near the functional axis or pivot point of the wearer's ankle include a shorter distance between the openings than is used in guides closer to the toe of the brace or higher up on the brace. This shorter distance increases the closing force in the area around the pivot point to help lock the ankle and foot into the brace.

In another aspect of the invention, the adjustable stirrup can be provided separately from the ankle brace. For example, an ankle brace having anchors (for anchoring on the separate adjustable stirrup) mounted thereon could be provided. An adjustable stirrup comprising a first rotatable tightening mechanism and lace system on a first end of the stirrup and a second rotatable tightening mechanism and lace system on a second end of the stirrup could then be attached to the ankle brace via the anchors. The adjustable stirrup may have a nonadjustable loop on the second end to be engaged into the ankle brace anchor while the first end retains the rotatable tightening mechanism for adjustment. The adjustable stirrup would operate independently of the ankle brace.

Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

We claim:

1. An ankle brace comprising:
   (a) a boot assembly comprising upper and lower portions and a semi-rigid or rigid support,
   (b) an adjustable stirrup configured to go under an arch of a wearer's foot, the adjustable stirrup being located at least partially within the boot assembly,
   (c) a first lace threaded through each end of the adjustable stirrup,
   (d) a first rotatable tightening mechanism configured to apply tension on the lace thereby tightening the adjustable stirrup and pulling it upward, wherein the first lace and first rotatable tightening mechanism are not configured to tighten the upper portion.

2. The ankle brace of claim 1 wherein the adjustable stirrup comprises a nylon strap.

3. The ankle brace of claim 1 wherein the boot assembly comprises a spacer fabric as a primary outer surface.

4. The ankle brace of claim 1 wherein the boot assembly comprises rip-stop nylon as a primary outer surface.

5. The ankle brace of claim 1 wherein the boot assembly comprises a nylon fabric of 70 denier or higher as a primary outer surface.

6. The ankle brace of claim 1 further comprising lace guides to guide the first lace to the adjustable stirrup and the first tightening mechanism.

7. The ankle brace of claim 1 wherein the first tightening mechanism is located on a back of the brace.

8. The ankle brace of claim 1 wherein the first tightening mechanism comprises a mechanism of release for disengaging the first tightening mechanism.

9. The ankle brace of claim 1 wherein the boot assembly comprises opposing sides having opposing lower lacing guides and the first lace is threaded through the lower opposing lacing guides on the lower opposing sides of the boot assembly such that when the first tightening mechanism applies tension on the first lace, the lower opposing lacing guides are advanced towards each other.

10. The ankle brace of claim 1 wherein the boot assembly comprises opposing sides having opposing lower lacing guides and a second lace is threaded through the lower opposing lacing guides on the lower opposing sides of the boot assembly such that when a second tightening mechanism applies tension on the second lace, the lower opposing lacing guides are advanced towards each other.

11. The ankle brace of claim 10, wherein the second tightening mechanism is located on a tongue configured to be positioned between the opposing sides of the boot assembly when the ankle brace is closed.

12. The ankle brace of claim 10 further comprising a tongue configured to be positioned between the opposing sides of the boot assembly when the ankle brace is closed.

13. The ankle brace of claim 1 further comprising a tongue configured to be positioned between opposing sides of the boot assembly when the ankle brace is closed.

14. The ankle brace of claim 1 wherein the support comprises a semi-rigid polymer.

15. The ankle brace of claim 1 wherein the support mimics an anchor and heel lock of conventional taping methods.

16. The ankle brace of claim 1, wherein the upper portion comprises opposing sides, and wherein the first lace and first rotatable tightening mechanism are not configured to draw the opposing sides together.

17. The ankle brace of claim 16, wherein the upper portion comprises opposing sides having upper opposing lacing guides and a second lace is threaded through the upper opposing lacing guides on the upper opposing sides of the boot assembly such that when a third tightening mechanism applies tension on the second lace, the upper opposing lacing guides are advanced towards each other.

18. The ankle brace of claim 1, wherein the upper portion of the boot assembly is the portion of the assembly configured to be above a functional axis of a wearer's ankle when worn.

* * * * *